US012605214B2

(12) United States Patent
Meurer et al.

(10) Patent No.: US 12,605,214 B2
(45) Date of Patent: Apr. 21, 2026

(54) ATLAS-BASED TRAJECTORY PLANNING

(71) Applicant: Brainlab SE, Munich (DE)

(72) Inventors: Yannic Meurer, Munich (DE);
Andreas Blumhofer, Munich (DE)

(73) Assignee: BRAINLAB SE, Munich (DE)

(*) Notice: Subject to any disclaimer, the term of this
patent is extended or adjusted under 35
U.S.C. 154(b) by 319 days.

(21) Appl. No.: 18/276,824

(22) PCT Filed: Feb. 17, 2022

(86) PCT No.: PCT/EP2022/053958
§ 371 (c)(1),
(2) Date: Aug. 10, 2023

(87) PCT Pub. No.: WO2023/155988
PCT Pub. Date: Aug. 24, 2023

(65) Prior Publication Data
US 2025/0000583 A1 Jan. 2, 2025

(51) Int. Cl.
*A61B 34/10* (2016.01)
*G06T 7/11* (2017.01)
*G06T 7/30* (2017.01)

(52) U.S. Cl.
CPC ................ *A61B 34/10* (2016.02); *G06T 7/11*
(2017.01); *G06T 7/30* (2017.01);
(Continued)

(58) Field of Classification Search
CPC ..... A61B 6/505; A61B 6/5229; A61B 8/0875;
A61B 8/5238; A61B 34/10;
(Continued)

(56) References Cited

U.S. PATENT DOCUMENTS

2017/0112575 A1* 4/2017 Li ........................... A61B 34/10
2024/0216067 A1* 7/2024 O'Connor .............. A61B 34/10

FOREIGN PATENT DOCUMENTS

WO 2017028934 A1 2/2017

OTHER PUBLICATIONS

Vijayan et al. "Automatic pedicle screw planning using atlas-based
registration of anatomy and reference trajectories." Physics in
Medicine & Biology 64.16 (2019): 165020. (Year: 2019).*

(Continued)

*Primary Examiner* — Katrina R Fujita
(74) *Attorney, Agent, or Firm* — Gray Ice Higdon

(57) ABSTRACT

Disclosed is a computer-implemented method of planning a
straight trajectory in a medical image of an anatomical
structure. A template of the straight trajectory is given in an
atlas and the atlas is registered with the medical image. The
atlas is divided into a first area and one or more second areas,
wherein the first area comprises the straight trajectory and
the one or more second areas do not comprise any part of the
straight trajectory. When the transformation of the atlas onto
the medical image is calculated, the first and second areas
are treated differently. The transformation of the first area
maintains the straight shape of the trajectory and is thus
restricted. The transformation of the one or more second
areas is unrestricted and thus allows any kind of image
registration. The template of the transformed atlas is the
applied to the medical image.

14 Claims, 6 Drawing Sheets

(52) U.S. Cl.
CPC ... *A61B 2034/102* (2016.02); *A61B 2034/107* (2016.02); *G06T 2207/30012* (2013.01)

(58) Field of Classification Search
CPC ........ A61B 2034/102; A61B 2034/105; A61B 2034/107; A61B 2576/00; G06T 7/11; G06T 7/30; G06T 2207/10081; G06T 2207/10088; G06T 2207/10116; G06T 2207/30012; G06T 2207/30241
See application file for complete search history.

(56) References Cited

OTHER PUBLICATIONS

Vijayan et al. "Automatic trajectory and instrument planning for robot-assisted spine surgery." Medical Imaging 2019: Image-Guided Procedures, Robotic Interventions, and Modeling. vol. 10951. SPIE, 2019. (Year: 2019).*

Han et al. "Atlas-based automatic planning and 3D-2D fluoroscopic guidance in pelvic trauma surgery." Physics in Medicine & Biology 64.9 (2019): 095022. (Year: 2019).*

Goerres J et al: "Spinal pedicle screw planning using deformable atlas registration", Physics in Medicine and Biology, 14 pages, dated Mar. 14, 2017.

Goerres J et al: "Planning, guidance, and quality assurance of pelvic screw placement using deformable image registration", Physics in Medicine and Biology, 4 pages, dated Nov. 13, 2017.

Hasan Al-Marzouqi et al: "Planning a safe drilling path for cochlear implantation surgery using image registration techniques", SPIE digital library, 4 pages, dated Mar. 22, 2007.

International Searching Authority, International Search Report and Written Opinion issued in Application No. PCT/EP2022/053958, 14 pages, dated Oct. 18, 2022.

* cited by examiner restricted
transformation

ATLAS-BASED TRAJECTORY PLANNING

FIELD OF THE INVENTION

The present invention relates to a computer-implemented method for planning a straight trajectory in a medical image of an anatomical structure, a corresponding computer program, a computer-readable storage medium storing such a program and a computer executing the program.

TECHNICAL BACKGROUND

It is often desired to plan a straight trajectory in a medical image of an anatomical structure, like an organ, of a bone or of a part thereof. The straight trajectory for example defines the path of an implant, a drill hole or a radiation beam. This planning can be aided by providing a prototype or template of the straight trajectory in an atlas of the anatomical structure. The atlas is a generic model of the anatomical structure. The atlas is matched to the medical image and the template of the straight trajectory in the matched atlas is applied to the medical image. This document relates to applying the transformed template of the straight trajectory to the medical image while assuring that the trajectory applied to the medical image is straight.

In this document, the template or model of the straight trajectory in the atlas is also simply referred to as straight trajectory in the atlas.

The present invention can be used for spinal planning procedures e.g. in connection with a system for spinal planning, such as Elements Spine Planning or Elements Alignment & Implants of Brainlab AG Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The general concept of the present invention is that the atlas which comprises the template of the straight trajectory is divided into a first area and one or more second areas, wherein the first area comprises the straight trajectory and the one or more second areas do not comprise any part of the straight trajectory. When the transformation of the atlas onto the medical image is calculated, the first and second areas are treated differently. The transformation of the first area maintains the straight shape of the trajectory and is thus restricted. The transformation of the one or more second areas is unrestricted and thus allows any kind of image registration.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of planning a straight trajectory in a medical image of an anatomical structure. The method comprises executing, on at least one processor of at least one computer (for example at least one computer being part of a navigation system), the following exemplary steps which are executed by the at least one processor.

In a (for example first) exemplary step, medical image data representing the medical image are acquired.

In a (for example second) exemplary step, atlas data representing an atlas comprising a representation of the anatomical structure are acquired, wherein a first area of the atlas data comprises a representation of the straight trajectory and at least one second area of the atlas data does not comprise any part of the straight trajectory.

In a (for example third) exemplary step, a transformation of the atlas data onto the medical image data is calculated, comprising a restricted transformation of the first area, wherein the restricted transformation is a transformation in which the straight trajectory in the atlas data remains straight, and an unrestricted transformation of the at least one second area.

In a (for example fourth) exemplary step, the straight trajectory of the transformed atlas data is applied to the medical image data.

The medical image acquired in the first step can be any two-dimensional or three-dimensional image acquired using a suitable imaging modality, such as x-ray, ultrasound, MRI or CT. The medical image data can further represent a sequence of multiple medical images captured at different points in time. This is also referred to as moving medical image. In the case of a moving medical image, the present invention can be implemented for a single medical image, multiple medical images or all medical images of the sequence.

The medical image represented by the medical image data shows an anatomical structure, such as an organ, a bone or a part thereof.

The atlas represented by the atlas data is a virtual or digital model of a creature and comprises at least a part of the anatomical structure for which the straight trajectory is to be planned. An atlas can for example be a medical image of the anatomical structure, or a part thereof, using the same imaging modality as the medical image, wherein the outline of the anatomical structure is marked in the atlas and the straight trajectory is also indicated in the atlas. The straight trajectory can be defined, for example, by a line drawn in the atlas or at least two points defined in the atlas. In one embodiment, the straight trajectory is defined by two points on the outline of the anatomical structure.

The atlas comprises a first area containing the representation of the straight trajectory. The first area can comprise the straight trajectory only or an additional area surrounding the straight trajectory, for example around the axial direction of the straight trajectory. This axial direction coincides with the straight trajectory or is parallel thereto. The first area can for example be cylindrical or have a cuboid shape.

The atlas further comprises at least one second area which does not comprise any part of the straight trajectory. The second area does for example comprise the rest of the anatomical structure as far as represented by the atlas data and can comprise more than the anatomical structure, for example the rest of the atlas data.

It shall be noted that the atlas data can have more than one first area and/or additional areas other than the first and second areas. The atlas can for example comprise a third area which does not comprise a template of a straight trajectory and for which the transformation is also limited, for example to rotations, translations and scaling. A second area can be formed by multiple sub-areas which do not necessarily have to be adjoining.

In this document, the terms "atlas" and "atlas data" as well as "medical image" and "medical image data", respectively, are used synonymously as long as it is not necessary to distinguish between them.

The third step of calculating a transformation of the atlas data onto the medical image data can also be referred to as (image) registration or matching of the atlas with the medical image. This transformation or registration treats the first area and the at least one second area differently. A restricted transformation is performed for the first area, wherein the restriction lies in the fact that the transformation is limited, or restricted, to transformations in which the straight trajectory remains straight. No such restriction is applied to the transformation of the at least one second data, which means that this transformation is unrestricted.

Any known and suitable algorithm or approach for performing a restricted or unrestricted transformation can be used. An example of a restricted transformation is a rigid transformation and an example of an unrestricted transformation is an elastic transformation.

Since the present invention defines a first area of the atlas data for which only a restricted transformation is allowed and at least one second area for which an unrestricted transformation is allowed, the transformation is also referred to as partly restricted transformation.

The fourth step of calculating the transformation can use multiple atlases, each of which is transformed onto the medical image. Each atlas comprises a template of a straight trajectory, and the final straight trajectory to be applied to the medical image is calculated from the plurality of transformed templates of the multiple atlases. Multiple approaches for calculating the final straight trajectory can be used, in analogy to the different approaches in multi-atlas segmentation.

In the fourth step, the straight trajectory is taken from the transformed atlas data and applied to the medical image data, which means that the straight trajectory is for example drawn into or overlayed over the medical image.

In the context of the present invention, it is sufficient that a surgeon plans the straight trajectory only once in the atlas and the straight trajectory is then transferred to the actual medical image. By providing the restricted transformation to the first area comprising the straight trajectory, it is guaranteed that the straight trajectory is not warped or bent during the transformation and the trajectory indicated in the medical image is thus also straight.

The transformation described herein can apply to less dimensions than the number of dimensions of the medical image and/or the atlas. If the atlas is two-dimensional and the medical image is three-dimensional, the atlas can be registered to a slice of the medical image data. If the atlas is three-dimensional and the medical image is two-dimensional, a slice of the atlas can be registered to the medical image data. If both the atlas and the medical image are three-dimensional, only a slice of the atlas can be registered to a slice of the medical image. Said slice of the atlas preferably lies in a plane in which the template of the straight trajectory lies.

In one embodiment, the restricted transformation allows a rotation in up to three rotational dimensions, a translation in up to three translational dimensions and a scaling along the axis of the straight trajectory. In this context, the axis means the longitudinal axis of the straight trajectory. Such a restriction guarantees that the straight trajectory remains straight.

It shall be noted that the scaling along the axis of the straight trajectory does not have to be uniform. The first area might be divided into several sections along the axis of the straight trajectory and each section could be scaled individually along the axis of the straight trajectory.

In one implementation, the restricted transformation further allows an identical scaling along two axes which are perpendicular to each other and perpendicular to the axis of the straight trajectory. In this implementation, the shape of the first area in a plane perpendicular to the axis of the straight trajectory remains identical and only its size is varied.

In one implementation, the restricted transformation further allows a shearing in direction parallel to the axis of the straight trajectory. This also guarantees to keep the straight trajectory straight.

In one embodiment, the method further comprises the step of adapting the length of the straight trajectory in the medical image data such that the end points of the straight trajectory lie on the surface of the anatomical structure in the medical image data.

For example due to the limitations to the transformation of the first area, the end points of the straight trajectory when applied to the medical image data might not lie on the boundary of the anatomical structure. With this embodiment, the length of the straight trajectory is adapted accordingly. It shall be noted that only the transformed straight trajectory might be scaled and/or shifted along its axis, but not the atlas data in the corresponding first area of the atlas data. The additional step of adapting the length of the straight trajectory is thus not part of the restricted transformation.

In one embodiment, the restricted transformation and the unrestricted transformation are performed with the boundary condition that the transformed atlas data is steady at a border between the first area and an adjoining second area. This results in smooth transition of the transformed atlas at said border.

The transformed atlas data being steady means that if points lying in the boundary surface between the first area and the adjoining second area are treated as belonging to both the first area and the adjoining second area, the restricted transformation and the unrestricted transformation of those points are identical or below a predetermined threshold, such as the distance between neighboring pixels or voxels of the atlas data or a fraction thereof.

In one implementation, the restricted transformation of the first area and the unrestricted transformation of the at least one second area are performed independently. For example, the restricted transformation of the first area is performed first and then the unrestricted transformation of the at least one second area is performed. This means that the restricted transformation and the unrestricted transformation can be optimized independently of each other. In an alternative implementation, a joint optimization of the restricted transformation and the unrestricted transformation is performed. In this case, each of the restricted transformation and the unrestricted transformation might not be optimal when seen alone, but the overall transformation of the atlas data onto the medical image data is optimized.

In one embodiment, the atlas data comprises representations of two straight trajectories and the atlas data comprises two first areas each comprising one of the two straight trajectories. A restricted transformation is performed on each of the two first areas.

In one implementation, the restricted transformations of the two first areas are performed independently of each other. In this implementation, the unrestricted transformation of the at least one second area can be completely independent of the restricted transformations or fulfil the boundary condition that the transformed atlas data is steady at a border between a first area and an adjoining second area as explained above.

In an alternative implementation, the restricted transformations of the two first areas are performed jointly. For example, the two first areas are considered as a common first area and only a single restricted transformation is calculated for the common first area.

In another example, the overall transformation comprising the restricted transformations of the two first areas and the unrestricted transformation of the at least one second area are optimized jointly. The explanation regarding the joint restricted and unrestricted transformations above applies in analogy.

In one embodiment, a second area is located between the two first areas and the restricted transformations of the two first areas and the unrestricted transformation of the second area located between the two first areas are performed with the boundary condition that the transformed atlas is steady at borders between the two first areas and the second area. The explanation of what is meant by "steady" given above applies here, too.

In one embodiment, a positional relationship between the two first areas, and thus between the two templates of the two straight trajectories, is maintained when calculating the transformation of the atlas data onto the medical image data. This can mean that the orientation between the two first areas is maintained. The distance between the two first areas might be maintained or varied.

This embodiment is particularly useful if the two straight trajectories in the two first areas are associated with each other, for example if they represent screws for fixing an implant or another object to a bone.

The two straight trajectories can be independent trajectories, for example of different implants, drill holes or beams. However, the two straight trajectories might be connected and therefore form a common trajectory, for example of an implant or an object in general which has a kink. The axes of the two trajectories are not parallel to each other, but might be identical. In this context, the term "connected" can mean that the two trajectories are consecutive, which means that one trajectory begins at the end of the other trajectory, the beginning of one trajectory lies between the two end points of the other trajectory or the two trajectories intersect with each other.

In one embodiment, the first area of the atlas data further comprises a virtual implant through which the axis of the first trajectory runs. There is thus not only the straight trajectory which presents the path of an implant, but also a visualization of the implant in terms of a virtual implant. In this embodiment, the first area preferably comprises at least the complete virtual implant and the at least one second area does not comprise any part of the virtual implant. Within this embodiment, it is particularly useful, but not mandatory, that the restricted transformation allows a rotation in up to three rotational dimensions, a translation in up to three translational dimensions and a scaling along the axis of the straight trajectory. It is further advantageous, but not mandatory, that the restricted transformation further allows identical scaling along two axis which are perpendicular to each other and perpendicular to the axis of the straight trajectory. In those cases, the shape of the virtual implant does not change, but only its size or, at most, its proportions.

In one implementation of this embodiment, the representation of the virtual implant after the restricted transformation is overlayed over or inserted into the medical image.

In one embodiment, the straight trajectory to be planned in the medical image is the trajectory of a screw, such as a transpedicular screw, and the virtual implant comprised in the corresponding first area of the atlas data is a representation of such a screw. A representation is for example an image or a drawing of an implant. The restricted transformation of the first area comprising the virtual screw means that the length and/or the diameter of the screw might change, but the general shape of the screw remains.

In one implementation, if the restricted information of the first area changes the length and/or the size of the virtual implant, a new virtual implant corresponding to the new length and/or size of the transformed virtual implant is selected, for example from a database, and applied to the medical image data. If, for example, the virtual implant is a screw and the length of the screw changes, the lead, or pitch, of the transformed screw no longer corresponds to the lead, or pitch, of a real screw. In this case, a representation of a real screw having the length of the transformed screw is selected and applied to the medical image data.

It is also possible that the atlas data comprises a type of implant rather than a virtual implant. In this case, the image of the implant to be added to or overlaid over the medical image is selected based on the type of implant, the restricted transformation and optionally the length of the transformed straight trajectory. If the type of implant is, for example, a transpedicular screw, then an image of a transpedicular screw having a length and a diameter according to the restricted transformation and the length of the transformed straight trajectory is acquired and applied to the medical image.

In one embodiment, the method further comprises the step of calculating an advance transformation of the atlas data onto the medical image data, wherein the advance transformation is performed before the transformation, and the step of segmenting the anatomical structure in the medical image data from the result of the advance transformation, wherein the transformation is performed onto the segmented anatomical structure in the medical image data.

It shall be noted that, in this embodiment, the term "transformation" means the transformation of the first exemplary step which comprises the restricted transformation of the first area and the unrestricted transformation of the at least one second area. The advance transformation is preferably an unrestricted transformation to achieve the best match of the atlas onto the medical image.

In this embodiment, segmenting the anatomical structure in the medical image data means finding the outline of the anatomical structure in the medical image data. Since the atlas also comprises the outline of the representation of the anatomical structure, the fact that the two outlines should coincide can be used as an additional boundary condition when calculating the transformation of the atlas data onto the medical image data in the third exemplary step. This is particularly advantageous if the advance transformation is unrestricted such that the optimum outline of the anatomical structure in the medical image is found.

In an alternative embodiment, the method further comprises the step of segmenting the anatomical structure in the medical image data using the transformed atlas data. In this alternative embodiment, the transformed atlas data is the result of the third exemplary step, and thus the result of the restricted transformation of the first area and the unrestricted transformation of the at least one second area. In this case, no advance transformation is required, but the result of the segmentation of the anatomical structure in the medical image data might be less accurate.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the fourth aspect;

b) at least one electronic data storage device storing at least the atlas data and the medical image data; and c) a medical device for carrying out a medical procedure on the patient, wherein the at least one computer is operably coupled to the at least one electronic data storage device for acquiring, from the at least one data storage device, at least the atlas data and the medical image data, and the medical device for issuing a control signal to the medical device for controlling the operation of the medical device on the basis of the position of the straight trajectory in the medical image data.

In particular, the control signal can be issued if the straight trajectory passes an predetermined area of the anatomical structure.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of placing an implant, drilling a hole or applying a treatment beam. More particularly, the invention does not involve or in particular comprise or encompass any surgical or therapeutic activity. The invention is instead directed as applicable to image data processing. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Computer-Implemented Method

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas/Atlas Segmentation

Preferably, atlas data is acquired which describes (for example defines, more particularly represents and/or is) a general three-dimensional shape of an anatomical structure, which is also refereed to as an anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image registration algorithm which conducts an image registration between the atlas data and the medical image data. The result of the comparison can be a measure of similarity between the atlas data and the medical image data. The atlas data comprises image information (for example, positional image information) which can be matched (for example by applying an elastic or rigid image registration algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Elastic Registration, Image Registration/Morphing, Rigid Registration

Image registration can be elastic image registration or rigid image registration. In the case of rigid image registration, the relative position between the pixels of a 2D image and/or voxels of a 3D image is fixed, while in the case of elastic image registration, the relative positions are allowed to change.

In this application, the term "image morphing" is also used as an alternative to the term "elastic image registration", but with the same meaning.

Elastic registration transformations (for example, elastic image registration transformations) are for example designed to enable a seamless transition from one dataset (for example a first dataset such as for example a first image or an atlas) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic registration transformation can for example be used to determine a degree of similarity (or similarity measure, see above) between the first and second datasets (first and second images). To this end, the deviation between the elastic registration transformation and an identity transformation is determined. The degree of deviation can for instance be calculated by determining the difference between the determinant of the elastic registration transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

In the examples described hereafter, two-dimensional views of an atlas and a medical image are used for illustrative purposes only. In general, the concept of the present invention is also applicable to three-dimensional atlas data and medical image data, and even four-dimensional medical image data representing a temporal sequence of 3D medical image data. In analogy, the invention is also applicable to a temporal sequence of 2D medical image data.

Figure 1:
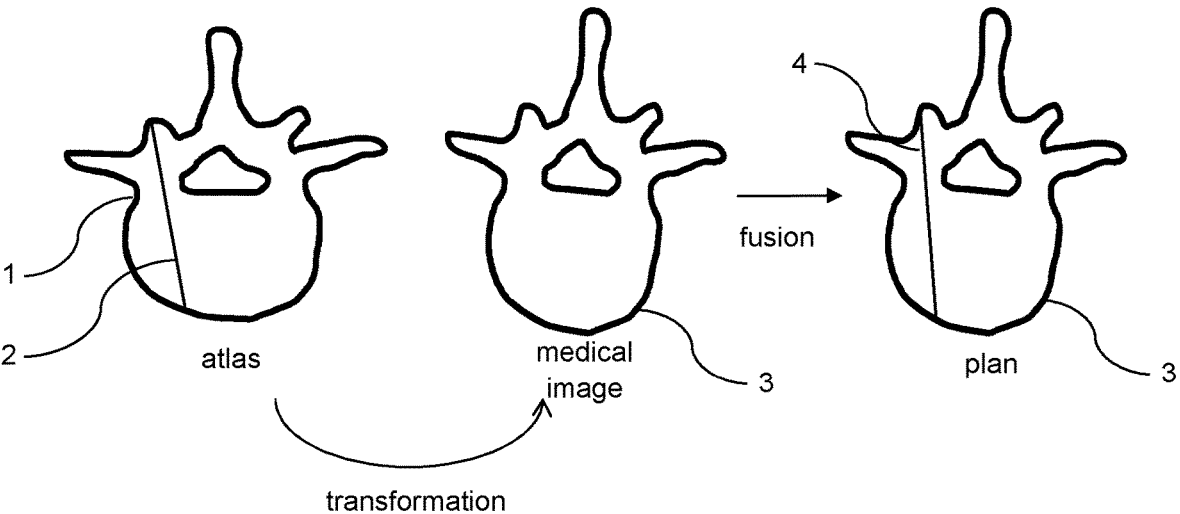
FIG. 1 illustrates the basic principle of applying a template from an atlas to a medical image.

FIG. 1 illustrates the basic principle of applying a template from an atlas to a medical image. In this example, the left part of FIG. 1 shows a view of an atlas comprising a representation of an anatomical structure in terms of a vertebra 1. The atlas further comprises a template of a straight trajectory 2.

The template of the straight trajectory 2 is a straight line which connects two points on the surface of the vertebra 1 and, in the present case, represents a part of a transpedicular screw to be placed in the vertebra. The template of the straight trajectory 2 for example represents the central axis of the transpedicular screw.

The central part of FIG. 1 shows a medical image of an anatomical structure in terms of a vertebra 3. The vertebra 1 of the atlas corresponds to the vertebra 3 shown in the medical image. As shown by the curved arrow, a transformation of the atlas onto the medical image is performed.

This transformation manipulates the atlas data such that the transformed representation of the vertebra 1 matches the vertebra 3 in the medical image as good as possible. This is also referred to as registration or matching. This transformation does not only transform the shape of the representation of the vertebra 1, but also the template of the straight trajectory 2.

In general, the transformation might result in a bent trajectory. But the present invention maintains the straight shape of the template of the straight trajectory 2 during registration. The transformed representation of the template of the straight trajectory 2 is referred to as straight trajectory 4 and applied to the medical image data. The straight trajectory 4 is drawn into or overlaid over the medical image of the vertebra 3. This step is also referred to as fusion because the transformed representation of the straight trajectory 2 is fused with the medical image of the vertebra 3 to arrive at a plan which is a combination of the medical image data and information taken from the transformed atlas.

Figure 2:
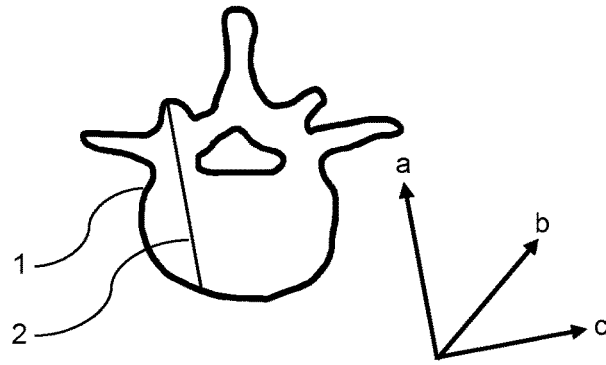
FIG. 2 shows directions assigned to a template of a straight trajectory.

FIG. 2 shows directions assigned to the template of the straight trajectory 2. The direction a is parallel to, or even coincides with, the straight trajectory. It is therefore also referred to as the longitudinal axis, or simply axis, of the template of the straight trajectory 2. The directions b and c are orthogonal to each other and to the axis a of the template of the straight trajectory 2.

Figure 3:
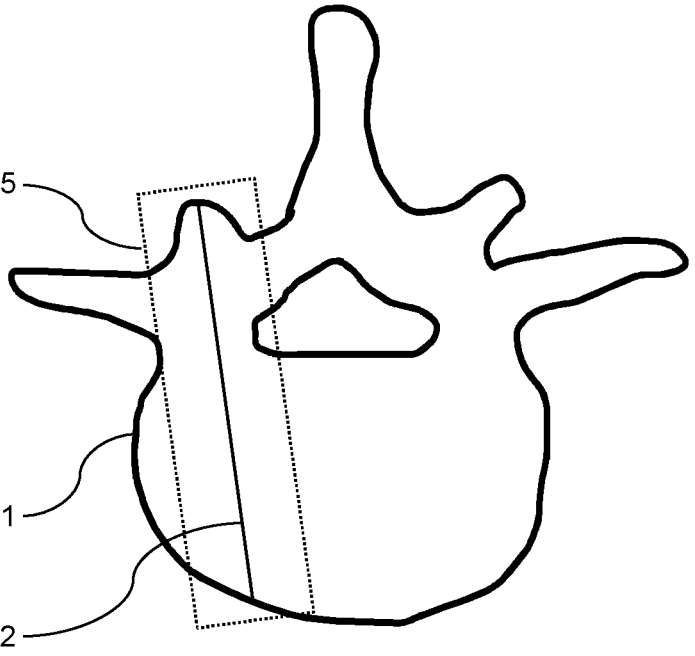
FIG. 3 shows a first area of an atlas.

FIG. 3 shows a first area 5 of the atlas of the vertebra 1. The first area 5 comprises the complete template of the straight trajectory 2. In the example shown in FIG. 3, the first area 5 is two-dimensional, but would have three dimensions for a three-dimensional atlas. In the three-dimensional case, the first area 5 is for example cylindrical, and the template of the straight trajectory 2 preferably, but not necessarily, coincides with the central axis of the cylindrical first area 5. The rest of the atlas of the vertebra 1 is referred to as second area. This second area does not comprise any part of the template of the straight trajectory 2.

Typically, an atlas is a two- or three-dimensional image comprising additional information, such as the template of the straight trajectory or other information, such as outlines of anatomical structures in order to enable a segmentation. But the atlas is not necessarily a two-dimensional area of pixels or a three-dimensional area of voxels. It could have any other structure, such as vector structure or a mesh structure.

According to the present invention, the transformation of the first area 5 is restricted such that the template of the straight trajectory 2 after the transformation is still straight. It lies within the scope of a skilled person to select a restricted transformation which keeps the template of the straight trajectory straight. One example of such a restricted transformation is a rigid transformation which allows a rotation of the first area 5 in up to three rotational dimensions, a translation of the first area 5 in up to three translational dimensions and a scaling of the first area 5 along the axis a of the template of the straight trajectory 2.

Figure 4:
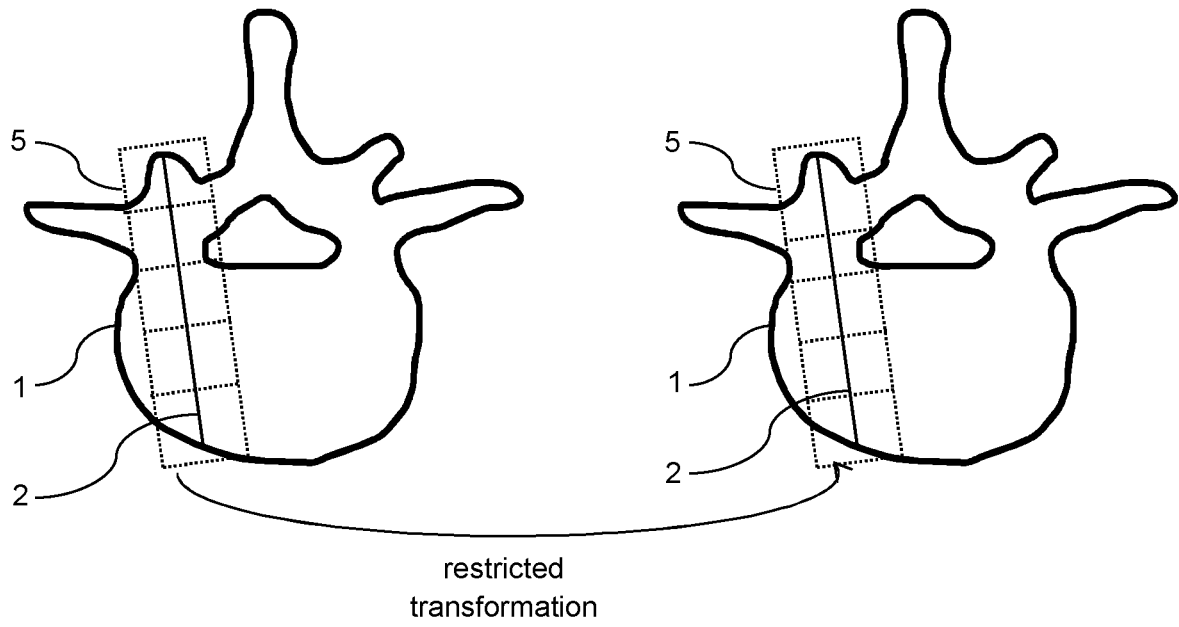
FIG. 4 shows a partly restricted transformation of the present invention.

As shown in FIG. 4, the scaling along the axis a of the template of the straight trajectory 2 is not necessarily uniform. In the example shown in FIG. 4, the first area 5 is divided into five sections along the axis a of the template of the straight trajectory 2. In each of those five sections, the scaling factor along the axis a of the template of the straight trajectory 2 can be chosen individually and independent of the other sections. Even with non-uniform scaling, the transformed template of the straight trajectory 2 is still straight.

Figure 5:
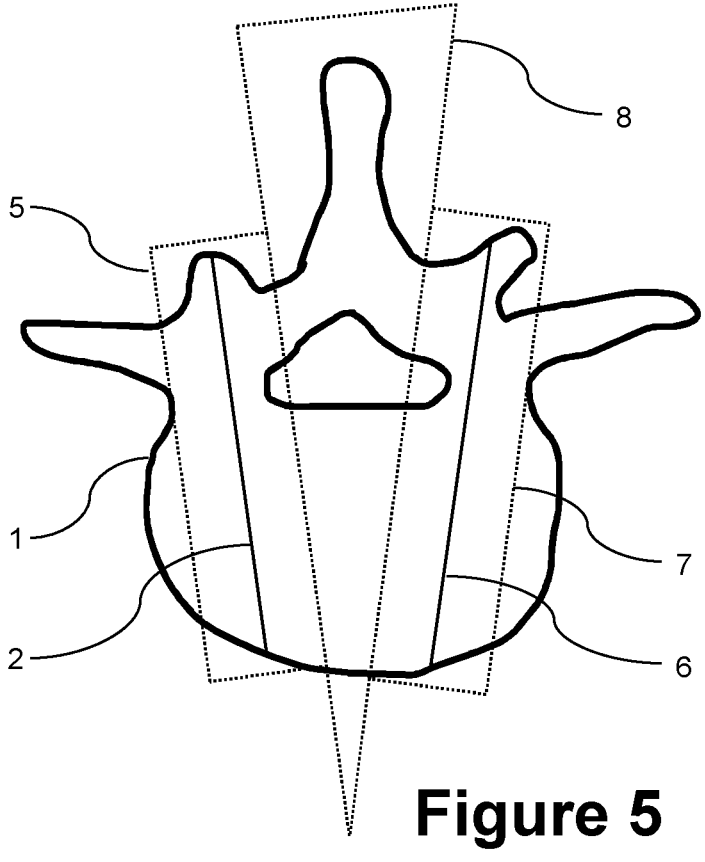
FIG. 5 shows an atlas with two first regions.

FIG. 5 shows the atlas of FIG. 3 with a second template of a straight trajectory 6, an additional first area 7 surrounding the second template of the straight trajectory 6 and a second area 8 located between the two first areas 5 and 7. As explained above, the first area 5 comprises the complete template of the straight trajectory 2, but no part of the second template of the straight trajectory 6, the additional first area 7 does not comprise any part of the template of the straight trajectory 2 and the second area 8 does not comprise any part of the template of the straight trajectory 2 or the second template of the straight trajectory 6. The second area 8 directly adjoints the first area 5 and the additional first area 7. Another second area, which is not shown in FIG. 5, covers at least the rest of the anatomical structure 1 in the atlas.

Figure 6:
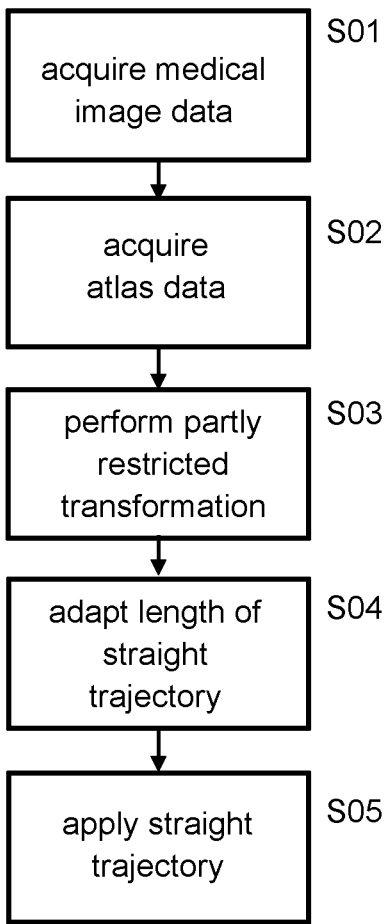
FIG. 6 shows a flow diagram of the present invention.

FIG. 6 shows a flow diagram of the method according to the present invention.

The method starts with step S01 in which the medical image data representing the medical image of the anatomical structure is acquired. In step S02, the atlas data is acquired. In the present examples, the medical image shows an anatomical structure in terms of the vertebra 3. In the present examples, the atlas data comprises a representation of the anatomical structure 1, which is a model of the vertebra 3.

In step S03, a partly restricted transformation of the atlas onto the medical image is performed. The partly restricted transformation is a restricted transformation of the first area(s) 5 and 7 and an unrestricted transformation of the at least one second area 8.

In the optional step S04, the length of the transformed straight trajectory is adapted. In the present example, the straight trajectory represents a part of a transpedicular screw. The template of the straight trajectory connects two points on the surface of the representation of the vertebra 1. So the transformed straight trajectory 4 in the plan shall also connect two points on the surface of the vertebra 3. In the optional step S04, the length of the straight trajectory 4 is adapted such that its end points lie on the surface of the vertebra 3. It shall be noted that this only applies to the straight trajectory 4 itself, but not to the atlas data of the corresponding first area. Step S04 is thus an additional step after calculating the partly restricted transformation.

In step S05, the template of the straight trajectory of the transformed atlas is applied to the medical image, which means that the transformed template of the straight trajectory is drawn into or overlaid over the medical image.

There are several options for calculating the partly restricted transformation in step S03.

In one embodiment, the restricted transformation of the first area 5 is calculated independently of the unrestricted transformation of the second area of the atlas. In this case, the optimum transformation for the first area and the second area, respectively, is found individually for each of the first and second areas. However, this might lead to a discontinuity of the transformed atlas data at the border between the first area and the second area. Another embodiment therefore sets the boundary condition that the transformed atlas data is steady, or continuous, at a border between the first area and an adjoining second area.

One exemplary implementation assigns atlas elements lying on the border between the first area 5 and an adjoining second area to both areas. In this document, an atlas element is a pixel if the atlas is a two-dimensional image, a voxel if the atlas is a three-dimensional image or a node if the atlas is a mesh of nodes.

In this implementation, the difference between the transformations of the same atlas element when belonging to the first area and the second area, respectively, must be below a predetermined threshold. This predetermined threshold can be an absolute value, such as zero, or depend on the pitch of the atlas elements in the atlas. It can for example be 0.1, 0.2 or 0.5 times the average distance of neighboring atlas elements.

In a variation of this implementation, not only atlas elements lying directly on the border between the first area 5 and the adjoining second area must fulfil this boundary condition, but also pixels in the vicinity of the border, which are pixels having a predetermined distance or less from this border. This predetermined distance can for example be 0.1, 0.2, 0.3 or 0.5 times the average distance of the atlas elements.

In one embodiment, the restricted transformation of the first area 5 is calculated first. The transformations of the atlas elements on the border of the first area, and optionally in the vicinity of the border of the first area, are then used as boundary conditions for the unrestricted transformation of the atlas elements of the second area on or in the vicinity of the border between the first area and the second area. The result of the restricted transformation therefore sets boundary conditions for the unrestricted transformation of the adjoining second area. However, the transformation of the second area is still unrestricted because, despite the boundary condition at the border to the adjoining first area, there are no limitations on the transformation.

In an alternative embodiment, the restricted transformation of the first area and the unrestricted transformation of the adjoining second area are calculated jointly. This means that the combination of the restricted transformation of the first area and the unrestricted transformation of the second area is optimized. The restricted transformation of the first area for example results in a first area similarity measure between the transformed first area and the corresponding part of the medical image and the unrestricted transformation results in a second similarity measure between the transformed second area and the corresponding part of the medical image. The restricted transformation and the unrestricted transformation are then by example calculated such that the (weighted) sum of the similarity measures or the product of the two similarity measures is maximized.

In the example shown in FIG. 5 in which the atlas data comprises two first areas 5 and 6, the restricted transformations of those two first areas can be calculated independently of each other or jointly. In the case of calculating the restricted transformations independently, each of the two first areas is independently matched to, or registered with, the medical image. The results of the two restricted transformations optionally define the boundary condition for the unrestricted transformation of the second area 8 such that the overall transformation of the atlas data is steady at the border between the first area 5 and the second area 8 and at the border between the additional first area 7 and the second area 8.

In an alternative embodiment, the restricted transformations of the first area 5 and the additional first area 7 are calculated jointly.

The two first areas 5 and 7 are for example considered as a single first area for which only a single restricted transformation is calculated. This single restricted transformation keeps the two templates of the two straight trajectories in the first area and the additional first area straight.

Figure 7:
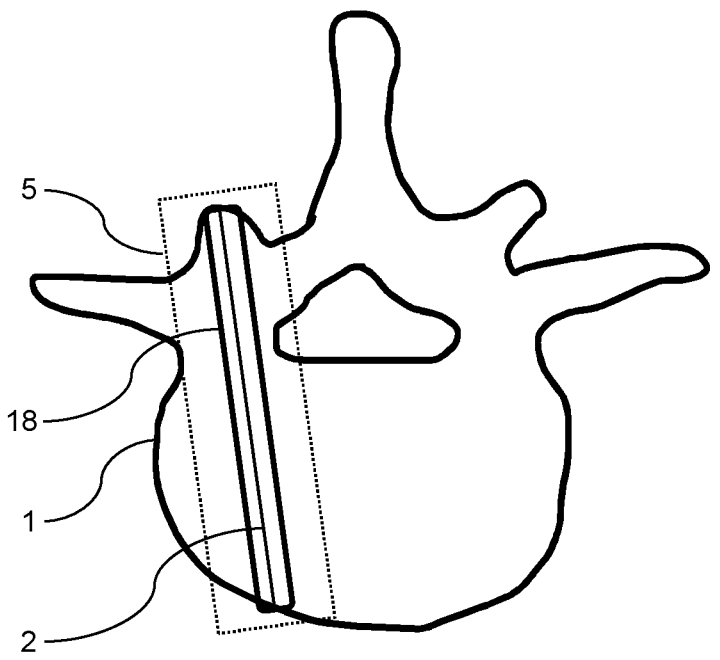
FIG. 7 shows atlas data with a virtual implant.

FIG. 7 shows an example of an atlas which does not only comprise a template of a straight trajectory 2, but also a virtual implant 18. In this embodiment, the virtual implant 18 is a graphical representation of an implant to be placed, in the present example of a transpedicular screw. This visualizes the implant in the atlas. The virtual implant 18 is completely comprised in the first area and thus undergoes the restricted transformation. This means that the shape of the virtual implant basically remains the same during the restricted transformation. In this embodiment, the transformed virtual implant is also applied to the medical image, for example by copying it into the medical image or overlaying it over the medical image.

The virtual implant 18 maintains its shape if the first area is only scaled along the axis a of the template of the straight trajectory 2. However, it also basically maintains its shape if it is identically scaled in the directions b and c. In the case of a transpedicular screw, an identical scaling along the directions b and c would change the diameter of the screw.

Figure 8:
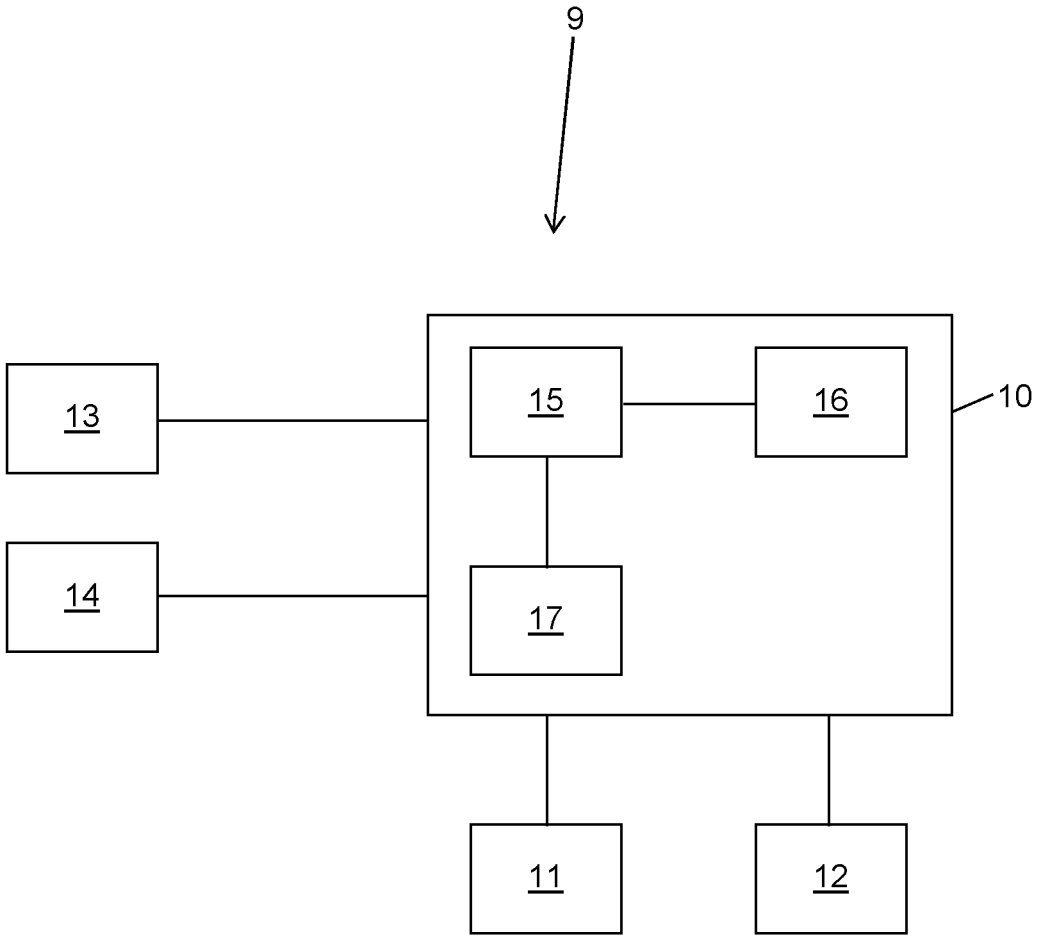
FIG. 8 shows a system for implementing the invention.

FIG. 8 schematically shows a system 9 for implementing the present invention.

The system 9 comprises a computer 10 connected to an input unit 11, such as mouse, keyboard, a touch-sensitive surface or a combination thereof, and an output unit 12, such as a monitor. The computer 10 is further connected to a medical imaging system 13 and a storage system 14. The medical imaging system 13 provides the medical image data representing the medical image and the storage system 14 provides the atlas data representing the atlas. The medical imaging system can be omitted, for example if the medical image data is already stored, for example in the storage system 14.

The computer 10 comprises a central processing unit 15, a memory 16 and an interface 17. The memory 16 stores program data for instructing the central processing unit 15 to carry out the present invention. The memory 16 can further store data acquired from external devices, such as the medical imaging system 13 or the storage system 14.

The interface 17 connects the computer to external devices, such as the input device 11, the output device 12, the imaging system 13 or the storage system 14.

The invention claimed is:

1. A computer-implemented method of planning a straight trajectory in a medical image of an anatomical structure, comprising:

acquiring medical image data representing the medical image, acquiring atlas data representing an atlas comprising a representation of the anatomical structure, wherein a first area of the atlas data comprises a representation of the straight trajectory and at least one second area of the atlas data does not comprise any part of the straight trajectory, calculating a transformation of the atlas data onto the medical image data, comprising a restricted transformation of the first area, wherein the restricted transformation applies a geometric constraint to the first area that preserves the straight shape of the straight trajectory in the atlas data, and an unrestricted transformation of the at least one second area, and applying the straight trajectory of the transformed atlas data to the medical image data.

2. The method of claim 1, wherein the restricted transformation allows a rotation in up to three rotational dimensions, a translation in up to three translational dimensions and a scaling along the axis of the straight trajectory.

3. The method of claim 2, wherein the restricted transformation further allows an identical scaling along two axes which are perpendicular to each other and perpendicular to the axis of the straight trajectory.

4. The method of claim 2 wherein the restricted transformation further allows a shearing in a direction parallel to the axis of the straight trajectory.

5. The method of claim 1 further comprising the step of adapting the length of the straight trajectory in the medical image data such that the end points of the straight trajectory lie on the surface of the anatomical structure in the medical image data.

6. The method of claim 1 wherein the restricted transformation and the unrestricted transformation are performed with the boundary condition that the transformed atlas data is steady at a border between the first area and an adjoining second area.

7. The method of claim 1 wherein the atlas data comprises representations of two straight trajectories and the atlas data comprises two first areas each comprising one of the two straight trajectories, wherein the restricted transformation is performed on each of the two first areas.

8. The method of claim 7, wherein a second area is located between the two first areas and the restricted transformations of the two first areas and the unrestricted transformation of the second area located between the two first areas are performed with the boundary condition that the transformed atlas is steady at borders between the two first areas and the second area.

9. The method of claim 7 wherein a positional relationship between the two first areas is maintained when calculating the transformation of the atlas data onto the medical image data.

10. The method of claim 1 wherein the first area of the atlas data further comprises a virtual implant through which the axis of the straight trajectory runs.

11. The method of claim 1 further comprising the steps of calculating an advance transformation of the atlas data onto the medical image data, the advance transformation being performed before the transformation, and of segmenting the anatomical structure in the medical image data from the result of the advance transformation, wherein the transformation is performed onto the segmented anatomical structure in the medical image data.

12. The method of claim 1 further comprising the step of segmenting the anatomical structure in the medical image data using the transformed atlas data.

13. A non-transitory computer readable medium comprising instructions which, when executed by a computer, causes the computer to acquire medical image data representing the medical image, acquire atlas data representing an atlas comprising a representation of an anatomical structure:

wherein a first area of the atlas data comprises a representation of a straight trajectory and at least one second area of the atlas data does not comprise any part of the straight trajectory, calculate a transformation of the atlas data onto the medical image data, comprising a restricted transformation of the first area, wherein the restricted transformation applies a geometric constraint to the first area that preserves the straight shape of the straight trajectory in the atlas data, and an unrestricted transformation of the at least one second area, and apply the straight trajectory of the transformed atlas data to the medical image data.

14. A system comprising at least one processor and associated memory, the memory storing instructions that when executed by the at least one processor cause the at least one processor to:

acquire medical image data representing the medical image, acquire atlas data representing an atlas comprising a representation of an anatomical structure, wherein a first area of the atlas data comprises a representation of a straight trajectory and at least one second area of the atlas data does not comprise any part of the straight trajectory, calculate a transformation of the atlas data onto the medical image data, comprising a restricted transformation of the first area, wherein the restricted transformation applies a geometric constraint to the first area that preserves the straight shape of the straight trajectory in the atlas data, and an unrestricted transformation of the at least one second area, and apply the straight trajectory of the transformed atlas data to the medical image data.

\* \* \* \* \*